(12) United States Patent
Matsushima et al.

(10) Patent No.: US 6,475,741 B1
(45) Date of Patent: Nov. 5, 2002

(54) NEUTROPHIL CHEMOTACTIC FACTOR CLONED CDNA AND MONOCLONAL ANTIBODIES THERETO

(75) Inventors: Kouji Matsushima; Teizo Yoshimura, both of Frederick; Edward J. Leonard, Chevy Chase; Joost Oppenheim, Bethesda; Ettore Appella, Chevy Chase; Stephen D. Showalter, Frederick, all of MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 10/037,218

(22) Filed: Nov. 9, 2001

Related U.S. Application Data

(62) Division of application No. 08/818,631, filed on Mar. 14, 1997, which is a division of application No. 07/169,033, filed on Mar. 16, 1988, now Pat. No. 5,652,338.

(51) Int. Cl.$^7$ .......................... C12Q 1/68; A61K 45/00; C07K 12/00; C12P 21/02; C12P 21/04
(52) U.S. Cl. .......................... 435/6; 424/85.1; 530/351; 435/69.5; 435/69.52
(58) Field of Search .................. 435/6, 69.5, 69.52; 424/85.1; 530/351

(56) References Cited

U.S. PATENT DOCUMENTS

| 4,714,674 A | 12/1987 | Palladino |
| 4,797,277 A | 1/1989 | Arfors |
| 4,897,348 A | 1/1990 | Johnson et al. |
| 5,306,627 A | 4/1994 | Yamada et al. |
| 5,401,643 A | 3/1995 | Yamada et al. |
| 5,451,399 A | 9/1995 | Gimbrone, Jr. et al. |
| 5,652,338 A | 7/1997 | Matsushima et al. |
| 5,698,196 A | 12/1997 | Matsushima et al. |
| 5,925,352 A | 7/1999 | Matsushima et al. |

FOREIGN PATENT DOCUMENTS

| EP | WO 89/04325 | 5/1989 |
| EP | WO 89/04836 | 6/1989 |
| EP | WO 89/10962 | 11/1989 |

OTHER PUBLICATIONS

Gregory et al., Biochemical and Biophysical Research Communications 151(2), pp. 883–90 (1988).
Walz et al., Biochemical and Biophysical Research Communications, vol. 149, No. 2, pp. 755–761 (1987).
Yoshimura et al., The Journal of Immunology, vol. 139, No. 3, pp. 788–793 (1987).
Tanaka et al., Fed. of European Biochem. Societies, vol. 236, No. 2, pp. 467–470 (1988).
Hickstein et al., Proc. Nat'l Acad. Sci. USA, vol. 86, pp. 257–261 (1989).
Schroder et al., The Journal of Immunology, vol. 139, No. 10, pp. 3474–3483 (1987).
Schmid et al., The Journal of Immunology, vol. 139, No. 1, pp. 250–256 (1987).
Yoshimura et al., Molecular Immunology, vol. 26, No. 1, pp. 87–93 (1989).
Yoshimura et al., Proc. Nat'l Acad. Sci. USA, Vol. 84, pp. 9233–9237 (1987).
Von Damme et al., J. Exp. Med., vol. 167, pp. 1364–1376 (1988).
Matsushima et al, J. Exp. Med., vol. 167, pp. 1883–1893 (1988).
Shimizu et al., Scand. J. Immunol. vol. 28, pp. 675–685 (1988).
Kownatzki, et al., Clin. Exp. Immunol., vol. 64(1), pp. 214–227 (1986).

Primary Examiner—Yvonne Eyler
Assistant Examiner—Janet L. Andres
(74) Attorney, Agent, or Firm—Morgan & Finnegan, L.L.P.; William S. Feiler; Dorothy R. Auth

(57) ABSTRACT

An isolated, synthetic preparation of a novel neutrophil-specific chemotactic factor (NCF), monoclonal antibodies having specific binding affinity for NCF and a clone containing the complete cDNA coding sequence for NCF are disclosed.

2 Claims, 5 Drawing Sheets

SEQUENCE LISTING

```
<160> NUMBER OF SEQ ID NOS: 2

<210> SEQ ID NO 1
<211> LENGTH: 1560
<212> TYPE: DNA
<213> ORGANISM: homo sapiens

<400> SEQUENCE: 1
ctccataagg cacaaacttt cagagacagc agagcacaca agcttctagg acaagagcca      60
ggaagaaacc accggaagga accatctcac tgtgtgtaaa catgacttcc aagctggccg     120
tggctctctt ggcagccttc ctgatttctg cagctctgtg tgaaggtgca gttttgccaa     180
ggagtgctaa agaacttaga tgtcagtgca taaagacata ctccaaacct ttccacccca     240
aatttatcaa agaactgaga gtgattgaga gtggaccaca ctgcgccaac acagaaatta     300
ttgtaaagct ttctgatgga agagagctct gtctggaccc caaggaaaac tgggtgcaga     360
gggttgtgga gaagttttg aagagggctg agaattcata aaaaaattca ttctctgtgg     420
tatccaagaa tcagtgaaga tgccagtgaa acttcaagca aatctacttc aacacttcat     480
gtattgtgtg ggtctgttgt agggttgcca gatgcaatac aagattcctg gttaaatttg     540
aatttcagta aacaatgaat agtttttcat tgtaccatga aatatccaga acatacttat     600
atgtaaagta ttatttattt gaatctacaa aaaacaacaa ataatttta aatataagga     660 ttttcctaga tattgcacgg gagaatatac aaatagcaaa attgggccaa gggccaagag     720
aatatccgaa ctttaatttc aggaattgaa tgggtttgct agaatgtgat atttgaagca     780
tcacataaaa atgatgggac aataaatttt gccataaagt caaatttagc tggaaatcct     840 ggatttttt ctgttaaatc tggcaaccct agtctgctag ccaggatcca caagtccttg     900
ttccactgtg ccttggtttc tcctttattt ctaagtggaa aaagtattag ccaccatctt     960
acctcacagt gatgttgtga ggacatgtgg aagcacttta agttttttca tcataacata    1020
```

-continued

```
aattattttc aagtgtaact tattaaccta tttattattt atgtatttat ttaagcatca    1080 aaatatttgtg caagaatttg gaaaaataga agatgaatca ttgattgaat agttataaag   1140
atgttatagt aaatttattt tattttagat attaaatgat gttttattag ataaatttca    1200
atcagggttt ttagattaaa caaacaaaca attgggtacc cagttaaatt ttcatttcag    1260
atatacaaca aataattttt tagtataagt acattattgt ttatctgaaa ttttaattga    1320
actaacaatc ctagtttgat actcccagtc ttgtcattgc cagctgtgtt ggtagtgctg    1380
tgttgaatta cggaataatg agttagaact attaaaacag ccaaaactcc acagtcaata    1440
ttagtaattt cttgctggtt gaaacttgtt tattatgtac aaatagattc ttataatatt    1500
atttaaatga ctgcattttt aaatacaagg ctttatattt ttaactttaa aaaaaaccgg    1560
```

<210> SEQ ID NO 2
<211> LENGTH: 72
<212> TYPE: PRT
<213> ORGANISM: homo sapiens

<400> SEQUENCE: 2

```
Ser Ala Lys Glu Leu Arg Cys Gln Cys Ile Lys Thr Tyr Ser Lys Pro
1               5                   10                  15

Phe His Pro Lys Phe Ile Lys Glu Leu Arg Val Ile Glu Ser Gly Pro
            20                  25                  30

His Cys Ala Asn Thr Glu Ile Ile Val Lys Leu Ser Asp Gly Arg Glu
        35                  40                  45

Leu Cys Leu Asp Pro Lys Glu Asn Trp Val Gln Arg Val Val Glu Lys
    50                  55                  60

Phe Leu Lys Arg Ala Glu Asn Ser
65                  70
```

NEUTROPHIL CHEMOTACTIC FACTOR CLONED CDNA AND MONOCLONAL ANTIBODIES THERETO

This application is a division of Ser. No. 08/818,631 filed Mar. 14, 1997, which is a division of Ser. No. 07/169,033 filed Mar. 16, 1988 now U.S. Pat. No. 5,652,338.

BACKGROUND OF THE INVENTION

1. Technical Field

The present invention relates to an isolated, synthetic preparation of a novel neutrophil-specific chemotactic factor (NCF), monoclonal antibodies having specific binding affinity for NCF and a clone containing the complete coding sequence for NCF.

2. State of the Art

Activated monocytes/macrophages produce various mediators that cause inflammation. Among them are chemotactic factors which cause white blood cells to migrate into inflammatory sites where these factors are released. Neutrophils, the dominant leukocytes attracted by the chemotactic factors, are believed to play a critical role in the inflammatory reactions. Such diseases as rheumatoid arthritis, idiopathic pulmonary fibrosis and certain pathological inflammatory changes in many other conditions are believed to be caused by neutrophils and/or their products. However, a specific pro-inflammatory mediator released by tissue macrophages and other cells in response to inflammatory stimuli and leading to neutrophil-rich leukocyte accumulation in host defense and disease, has not heretofore been identified and isolated.

SUMMARY OF THE INVENTION

It is, therefore, an object of the present invention to provide a biologically active novel synthetic polypeptide acting as a neutrophil-specific chemotactic factor (NCF).

It is a further object of the present invention to provide a molecular clone containing the complete coding sequence for the synthesis of NCF by either prokaryotic or eukaryotic expression vectors.

It is a still further object of the present invention to provide monoclonal antibodies having specific binding affinity for NCF of the present invention.

It is another object of the present invention to provide a kit comprising a container containing the cDNA for NCF quantitation, detection or localization of NCF mRNA in a body sample.

It is yet another object of the present invention to provide a kit comprising a container containing anti-NCF antibodies having specific binding affinity for NCF for quantitation, detection or localization of NCF in a body sample.

Other objects and advantages will become evident from the following detailed description of the invention.

BRIEF DESCRIPTION OF THE DRAWINGS

These and other objects, features and many of the attendant advantages of the invention will be better understood upon a reading of the following detailed description when considered in connection with the accompanying drawings wherein.

Figure 1:
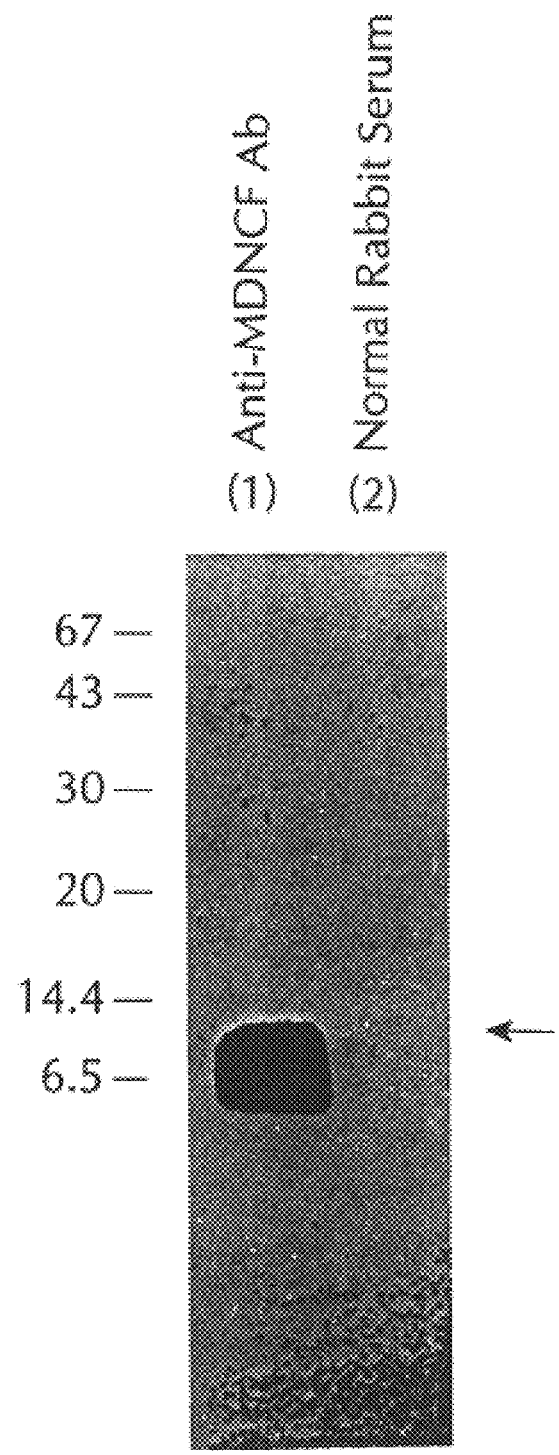
FIG. 1 demonstrates translation of cDNA into NCF protein in reticulocyte lysate system.
Figure 2A:
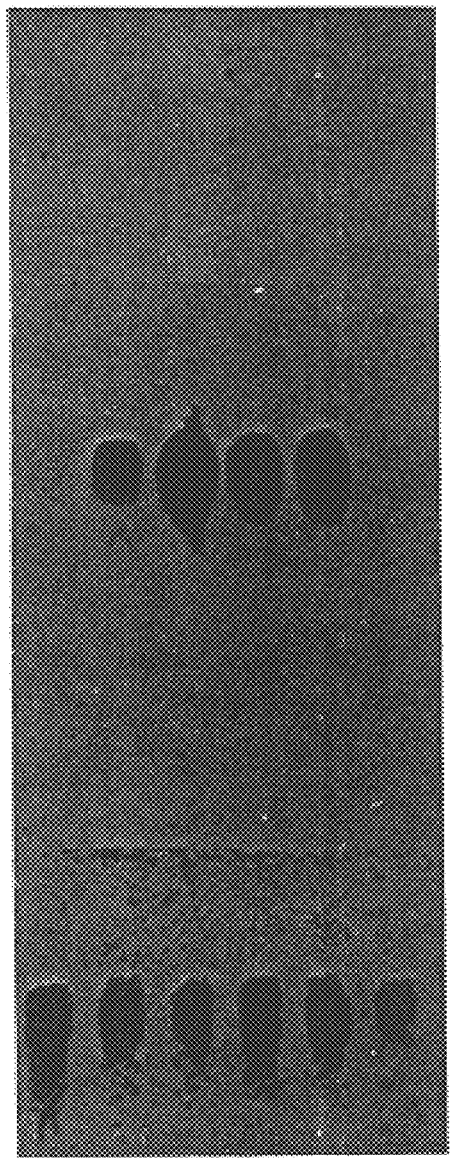
FIG. 2 shows.
Figure 2B:
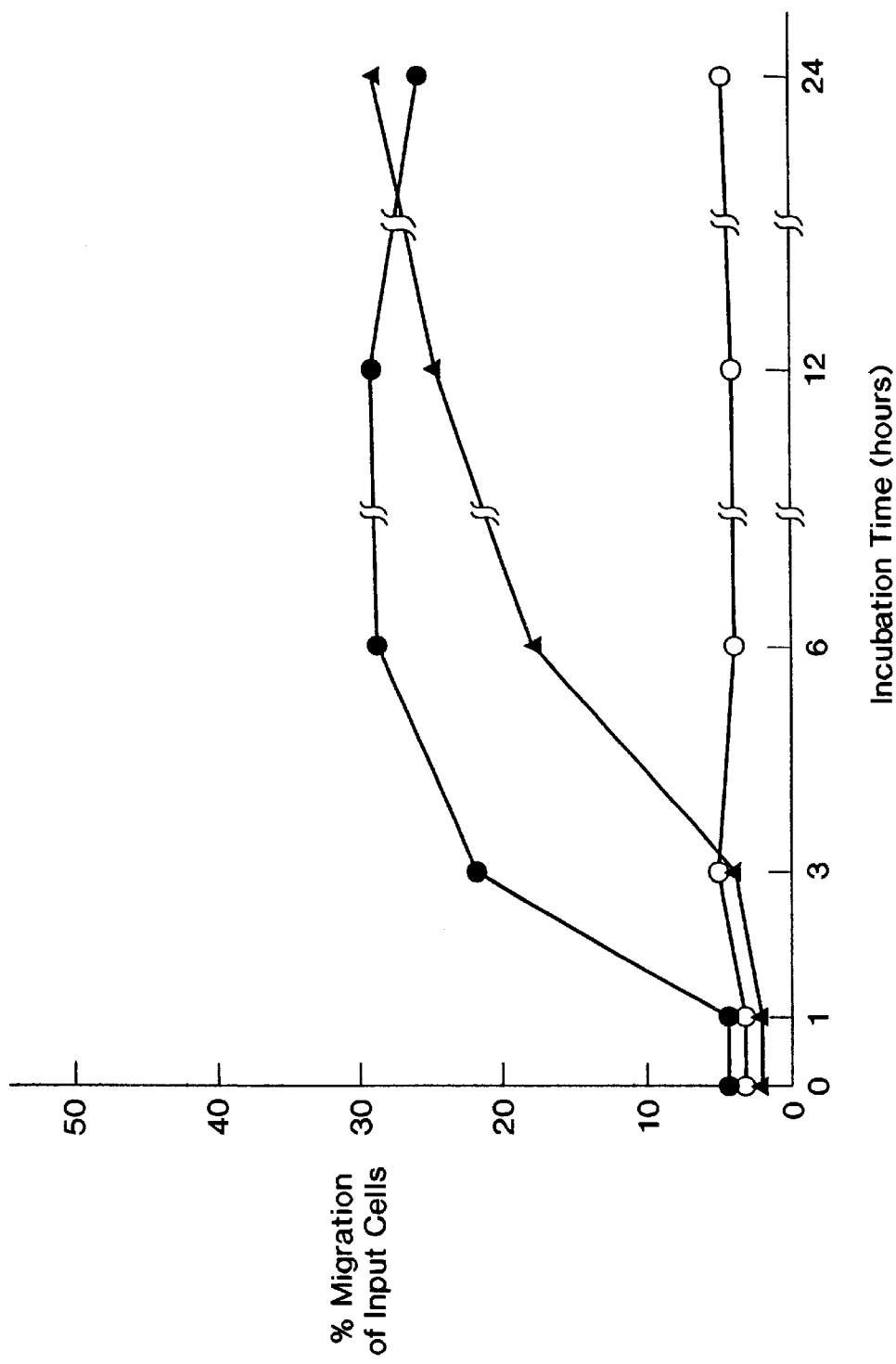
Figure 2C:
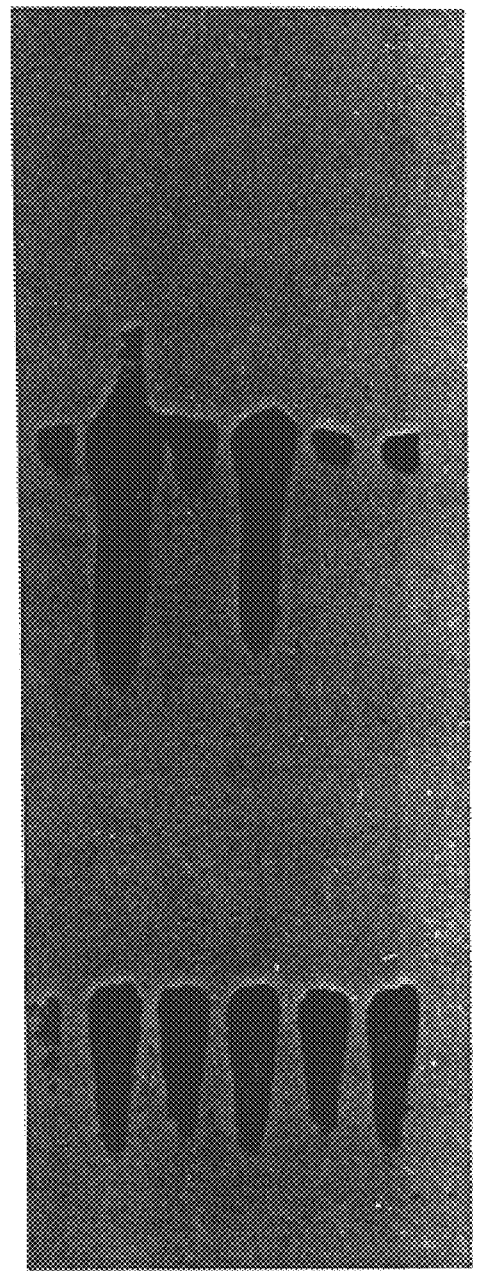
Figure 2D:
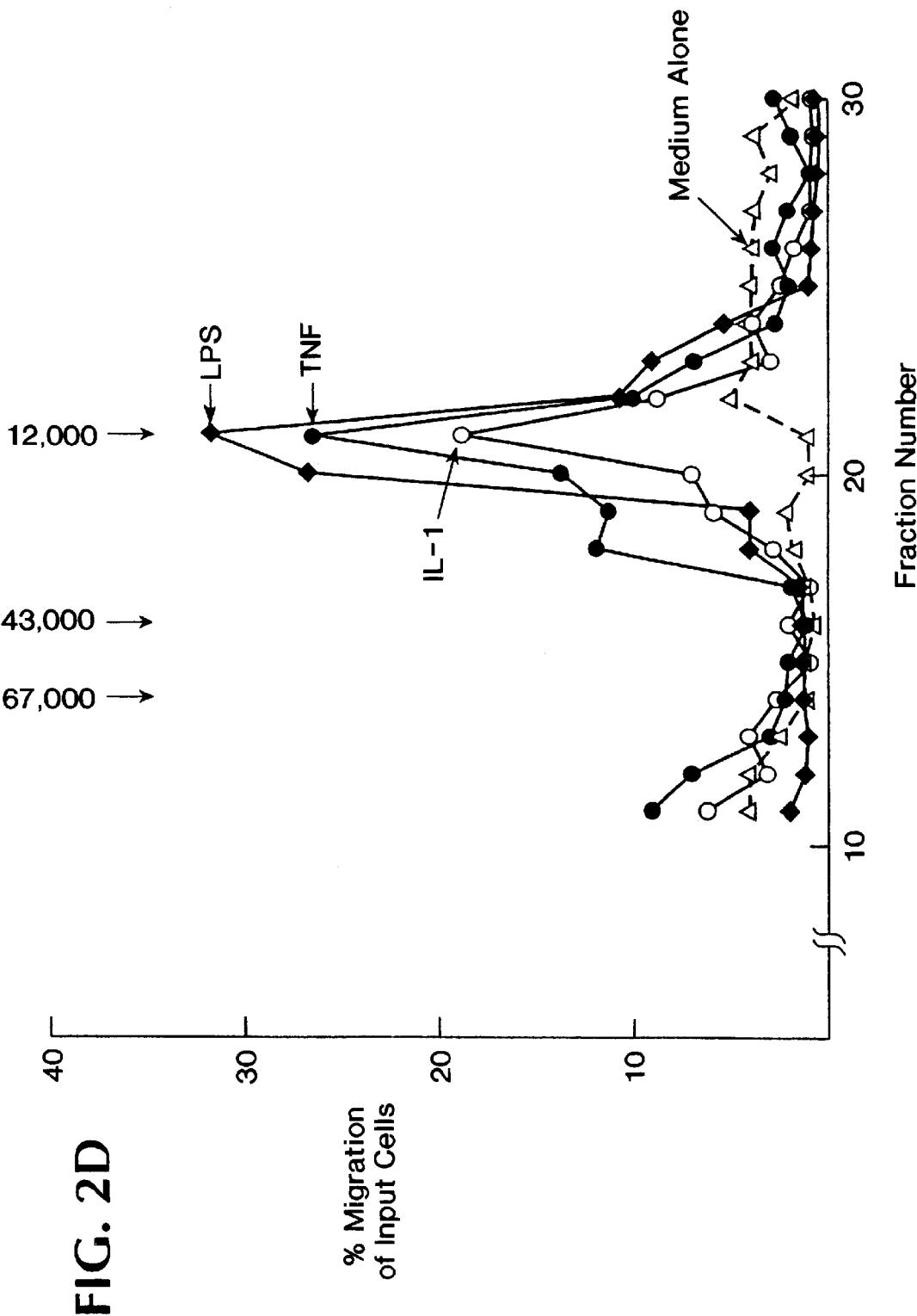

(a) Northern blot analysis of mRNA induction in lipopolysaccharide (LPS) stimulated peripheral blood mononuclear cells (PBMC);

(b) The time course of the accumulation of neutrophil chemotactic activity in culture media of PBMC after stimulation with LPS;

(c) Induction of NCF mRNA in PBMC by IL 1 or TNF, but not by IL 2, gamma-IFN, and alpha-IFN;

(d) HPLC gel filtration analysis of IL 1 and TNF induced neutrophil chemotactic activity.

DETAILED DESCRIPTION OF THE INVENTION

The above and various other objects and advantages of the present invention are achieved by a homogeneously pure, isolated, synthetic neutrophil chemotactic protein, designated herein NCF, composed in the whole or in part only of the following amino acid sequence (single letter code):

$NH_2$-S-A-K-E-L-R-C-Q-C-I-K-T-Y-S-K-P-F-H-P-K-F-I-K-E-L-R-V-I-E-S-G-P-H-C-A-N-T-E-I-I-V-K-L-S-D-G-R-E-L-C-L-D-P-K-E-N-W-V-Q-R-V-V-K-F-L-K-R-A-E-N-S (SEQ ID NO:2)

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed herein are standard methodologies well known to one of ordinary skill in the art.

Chemical synthesis of the NCF of the present invention composed of the 72 amino acid residues as shown above, is achieved by commercially available polypeptide synthesizers. Alternatively, the NCF of the present invention is synthesized by standard techniques employing an expression vector containing in its genome the cloned complete coding sequence of NCF. Anti-NCF monoclonal antibodies of the present invention are prepared by standard hybridoma technology and utilized for purification and assaying purposes following standard immunological methodologies well known in the art.

High performance liquid chromatography (HPLC), in situ hybridization assays, Northern blotting analyses and the like are typical examples of the standard conventional techniques well known to one of ordinary skill in the art, which can be employed for isolation, localization, differentiation, detection, or measurement of the mRNA for NCF in biological samples.

It should be noted that the fact that chemically synthesized polypeptide of the present invention at 10 nanomolar concentrations acts as a neutrophil attracting factor, is shown by the results in Table 1.

TABLE 1

Chemotactic response of human neutrophils to chemically synthesized NCF.

| Concentration of NCF, nanomolar | Percentage of assay neutrophils that migrated |
|---|---|
| 1000 | 23 |
| 100 | 34 |
| 10 | 32 |
| 1 | 5 |
| 0.1 | 1 |

TABLE 1-continued

Chemotactic response of human neutrophils to chemically synthesized NCF.

| Concentration of NCF, nanomolar | Percentage of assay neutrophils that migrated |
|---|---|
| Hanks medium | 0.3 |
| $10^{-7}$M fMet–Leu–Phe | 40 |

1. It is typical for chemoattractant dose-response curves to show an optimum, with a decreased response at concentrations above the optimum.
2. fMet-Leu-Phe is a commonly used reference chemoattractant.

It may be pointed out that various stimuli cause the release or secretion of more than one chemoattractant. Without the cDNA of the present invention, it is clear, of course, that the presence, specifically of the mRNA for NCF as an involved factor in a particular clinicopathological situation, could not be definitively identified and diagnosed. cDNA of the present invention due to its binding affinity for mRNA for NCF, for the first time makes it possible to analyze body samples such as joint fluid, sputum, alveolar lavage fluid, tissue samples and the like to detect the presence or absence of mRNA for NCF. Of course, the antibodies can also be utilized for diagnostic purposes to detect the NCF and to neutralize the NCF for alleviating any disease or anomalous conditions in which the presence of NCF is found to be a causative factor.

A pharmaceutical composition for use in treating inflammatory condition comprises an anti-inflammatory effective amount of the anti-NCF monoclonal antibodies in pharmaceutically acceptable carrier, such as physiological saline, sterile non-toxic buffer and the like.

A deposit of cDNA for NCF and of the hybridoma for anti-NCF monoclonal antibodies have been made at the ATCC, 10801 University Boulevard, Manassas, Va. 20110-209 on Jan. 12, 1988 and Feb. 17, 1988, respectively, under the accession numbers 40412 and HB9647, respectively. The deposits shall be viably maintained, replacing if they became non-viable, for a period of 30 years from the date of the deposit, or for 5 years from the last date of request for a sample of the deposit, which is longer, and made available to the public without restriction in accordance with the provisions of the law. The Commissioner for Patents and Trademarks, upon request, shall have access to the deposits.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A kit for determining the level of NCF mRNA-present in a sample, comprising a container containing cDNA for NCF for performing assay to determine the level of mRNA for NCF in a biological sample.

2. A method for detecting the level of mRNA for NCF in a sample, comprising reacting said sample with cDNA and determining the occurrence of hybridization by any conventional technique, the presence of said cDNA-mRNA hybrids being indicative of the presence of mRNA for NCF in said sample.

* * * * *